United States Patent
Khodarev et al.

(10) Patent No.: US 10,561,708 B2
(45) Date of Patent: *Feb. 18, 2020

(54) ANTI-TUMOR THERAPY

(71) Applicant: The University of Chicago, Chicago, IL (US)

(72) Inventors: Nikolai Khodarev, Villa Park, IL (US); Ravi Sood, Seattle, WA (US); Bernard Roizman, Chicago, IL (US); Ralph R. Weichselbaum, Chicago, IL (US)

(73) Assignee: The University of Chicago, Chicago, IL (US)

( * ) Notice: Subject to any disclaimer, the term of this patent is extended or adjusted under 35 U.S.C. 154(b) by 2 days.

This patent is subject to a terminal disclaimer.

(21) Appl. No.: 15/975,396

(22) Filed: May 9, 2018

(65) Prior Publication Data

US 2018/0256678 A1 Sep. 13, 2018

Related U.S. Application Data

(63) Continuation of application No. 14/901,929, filed as application No. PCT/US2014/043775 on Jun. 24, 2014.

(60) Provisional application No. 61/842,045, filed on Jul. 2, 2013.

(51) Int. Cl.
*A61K 38/17* (2006.01)
*A61K 31/506* (2006.01)
*A61K 45/06* (2006.01)

(52) U.S. Cl.
CPC .......... *A61K 38/177* (2013.01); *A61K 31/506* (2013.01); *A61K 45/06* (2013.01)

(58) Field of Classification Search
CPC .................................................... A61K 38/177
See application file for complete search history.

(56) References Cited

U.S. PATENT DOCUMENTS

2005/0277680 A1 12/2005 Priebe et al.
2006/0030536 A1 2/2006 Yu et al.
2007/0232668 A1 4/2007 Priebe et al.

FOREIGN PATENT DOCUMENTS

WO WO2011/069141 A2 6/2011
WO WO2012/151562 A1 11/2012

OTHER PUBLICATIONS

Hotte et al., Current management of castrate-resistant prostate cancer, 2010, Current Oncology, vol. 17, Suppl.2, pp. S72-S79 (Year : 2010).*
Shodeinde et al., Potential use of STAT2 inhibitors in targeted prostate cancer therapy: future prospects, 2012, Onco Targets and Therapy, 5, pp. 119-125 (Year: 2012).*
Barton et al., IL-6 signaling by STAT3 participates in the change from hyperplasia to neoplasia in NRP-152 and NRP-154 rat prostatic epithelial cells, 2001, BMC Cancer, 1:19 (Year: 2001).*
Bolla et al, Combined hormone therapy and radiation therapy for locally advanced prostate cancer, 2012, Critical Reviews in Oncology/Hematology, 84, e30-e34.
International Search Report and Written Opinion of the International Searching Authority issued in PCT Application No. PCT/US14/43775, dated Oct. 10, 2014.

* cited by examiner

*Primary Examiner* — Jeffrey S Lundgren
*Assistant Examiner* — Tori Strong
(74) *Attorney, Agent, or Firm* — McDonnell Boehnen Hulbert & Berghoff LLP (57) ABSTRACT

Compositions, kits and methods for treating cancer in a subject in need thereof are disclosed involving one or more inhibitors of the JAK/STAT pathway which renders the cancer chemosensitive and/or radiosensitive.

17 Claims, 4 Drawing Sheets

Figure 1. Activation of Jak/Stat signaling in PC3 xenografts by IR

Figure 3. Jak2 inhibitor TG-101348 (SAR302503) suppresses growth and sensitizes CW22RV1 xenografts to ionizing radiation

ANTI-TUMOR THERAPY

CROSS REFERENCE TO RELATED APPLICATIONS

This application is a continuation of U.S. application Ser. No. 14/901,929, filed Dec. 29, 2015, which is a U.S. National Stage of International Application No. PCT/US2014/043775, filed Jun. 24, 2014, which claims priority to U.S. Provisional Application No. 61/842,045, filed Jul. 2, 2013, the disclosures of which are hereby incorporated by reference in their entireties.

STATEMENT CONCERNING GOVERNMENT INTEREST

Not applicable

BACKGROUND OF THE INVENTION

1. Field of the Invention

The present invention relates to the identification and control of the JAK/STAT pathway for treatment of cancers, including chemoresistant and/or radioresistant cancers.

2. Description of the Background of the Invention

Prostate cancer is the second leading cause of cancer-related death in men with more than 28,000 Americans dying annually. In order for a cancer to be "successful" in the host it must survive typical oncogenic processes, as well as treatment regimens including iatrogenic insults, including androgen ablation, the more recently approved potent androgen receptor (AR) targeted agents, and often radiotherapy and taxane-based chemotherapy as well. A locally advanced prostate cancer and metastatic castrate resistant prostate cancer (mCRPC) also regularly develop resistance to the cytotohic host microenvironment and genotoxic anti-tumor therapy.

Just as importantly, prostate cancer tends to metastasize to bone, leading to significant morbidity and functional limitations prior to its lethal effects. Despite this burden, it is a cancer for which a number of localized and systemic therapies are available and in fact is an example of the success of molecular targeted oncologic treatment. More specifically, it was recognized more than half a century ago that prostate cancer is driven by the androgen receptor (AR) and this has led to the recent development of several more potent androgen receptor pathway directed therapies to supplement traditional surgical or medical castration. In addition to androgen receptor targeted treatments, more traditional DNA and DNA-repair targeted therapies have also been shown to be modestly effective in improving survival or ameliorating symptoms in this disease including the tubule targeted agents docetaxel and cabazitaxel, and radiotherapy with alpha ($Ra^{233}$), beta ($Sr^{89}$), and gamma (photon) particles.

The mortality burden nevertheless emphasizes the fact that these therapies are not curative and that this cancer continually evolves a resistant phenotype, which is broadly categorized as metastatic castrate-resistant prostate cancer (mCRPC), and which is ultimately the lethal phenotype. Aggressive prostate cancer is resistant to cytotoxic stimuli of microenvironment and uses yet elusive mechanisms to colonize distant sites. Although these events are likely to be important in many, if not all, human cancers, the relatively long natural history of prostate cancer and the variety of therapies typically utilized suggest that such adaptation is especially relevant to mCRPC and may use unique pathways.

Further advances in the treatment of prostate cancer, and especially systemic therapy of advanced local disease and mCRPC, must therefore take into account and target the fundamental survival pathways that the resistant cell utilizes. This concept has been previously applied to various investigational therapeutic approaches by attempting to target apoptosis, necrosis, and autophagy pathways as the presumptive final common pathway(s) for cellular death. To date these have met with only limited success, which may be due to the non-specific nature of the targeting agents, the multiple death pathways cells can follow, and the likelihood that activated survival pathways are context specific to tumor type and histology.

Targeting survival pathways in conjunction with traditional cytotoxic therapies has been previously attempted and continues to be an area of therapeutic investigation. Elucidation of the significance and role of the JAK/STAT pathway in oncogenesis is an area of fundamental and translational research as well and has been identified as altered in multiple epithelial malignancies. Furthermore, JAK targeted therapy is being investigated for the treatment of myeloproliferative diseases. For example, Ruxolitinib (INCB018424, trade names Jakafi® and Jakavi®, by Incyte Pharmaceuticals and Novartis, CAS 941678-49-5) was developed for the treatment of intermediate or high-risk myelofibrosis, a type of bone marrow cancer. It is also being investigated for the treatment of lymphomas and pancreatic cancer, polycythemia vera, and plaque psoriasis. However, the JAK/STAT pathway is not being investigated in prostate cancer as a potentially targetable survival pathway for which inhibition, in conjunction with other lethal insults, may be clinically pragmatic. Further, a number of mCRPC treatments targeting various androgen receptor and non-androgen receptor pathways are in development, but are expected to be limited by the fundamental activation of specific survival pathways in this disease.

While the importance of the JAK/STAT pathway, in general, for cancers continues to be investigated, the role it plays in tumors remains undefined. Consequently, there is an urgent and definite need to identify therapies that may potentially have a role in tumor development associated with the JAK/STAT pathway. Such therapies may provide new treatments for JAK/STAT-related cancers, and/or therapies targeted to the sensitization of cancers for chemotherapies and/or radiotherapies. Targeting JAK/STAT could thus inhibit a fundamental property of the malignant phenotype and open the door to multiple therapies, including combination therapy. Therefore, there is a need to determine the role of the JAK/STAT pathway in cancer, including solid tumors, which may play a role in developing effective new therapies for treating cancers around the JAK/STAT pathway. There is also a need to determine the most relevant members of the JAK/STAT signaling pathway for the survival cancer phenotype, leading to the identification of the most relevant target(s), and the most promising predictive biomarker(s). More effective and targeted cancer therapies with potentially fewer side effects are also needed.

SUMMARY OF THE INVENTION

A first aspect of the invention provides a method of treating a subject with a chemoresistant or radioresistant prostate cancer. The method comprises administering a therapeutically effective amount of an inhibitor of a JAK/STAT pathway to the subject.

In another embodiment, the cancer is associated with activation of a JAK/STAT-related pathway.

Illustratively, JAK includes a JAK1, a JAK2, a JAK3 or a Tyk2 kinase, and the STAT includes a STAT1, a STAT2, a STAT5, a STAT4, a STAT5, or a STAT6 transcriptional factor In one embodiment, the inhibitor of the JAK/STAT pathway inhibits at least one of a JAK, and consequently at least one of a STAT.

In another embodiment, the prostate cancer has an amplified level of MCL1 or LGP2 (DHX58) or immunoproteasome subunits PSMB8, 9, 10 expression as compared to a normal control cell.

DESCRIPTION

Treatment of a cancer in a subject in need thereof is provided herein, as are compositions, combinations, kits, and methods for treating cancer, and methods for identifying inhibitors of the JAK/STAT pathway having a role in the treatment of cancer and therapies to treat cancer based on this pathway. A JAK/STAT dependent cancer may include any solid tumor, including lung, prostate, head and neck, breast and colorectal cancer, melanomas and gliomas, and the like. While the present disclosure may be embodied in different forms, several specific embodiments are discussed herein with the understanding that the present disclosure is to be considered only an exemplification and is not intended to limit the invention to the illustrated embodiments.

JAK kinases are associated with a variety of cytokine and growth factor receptors, and signal through several downstream STAT homologs; however, the specific signaling pathways are quite complex and difficult to predict from disease to disease. For example receptors that are known to operate predominantly through JAK-dependent activation of a specific STAT protein, such as STAT1 through IFN-γ receptor activation or STAT3 through IL6/IL6R receptor gp130 activation can cross-activate alternative STAT5. This may occur through JAK cross-phosphorylation as has been demonstrated in the context of IFN-γ signaling in which cross phosphorylation of JAK1 and JAK2 has been demonstrated. Additional complexities of the JAK/STAT signaling pathway are introduced by the extensive interactions between different STATs. For example, STAT1 and STAT3 can form heterodimers both in the phosphorylated and non-phosphorylated forms. Further, STAT1 and STAT3 can both bind to the same promoter sequences of the same genes (including oncogenes MUC1 and MCL1). Therefore, although the JAK/STAT signaling pathway may have been previously described in other diseases including some specific cancers, the correlation to other diseases and cancers and its complex interactions cannot be readily ascertained by reference only to this other previously described disease or cancer.

The interactions between JAK and STAT components of this signaling pathway are complex. The development of small molecules and peptide inhibitors of individual JAK kinases and STAT proteins is rather rapid. Therefore, it is important to evaluate functional consequences of the inhibition of individual members of this cascade in a target cancer for which the effects have not been determined such as in prostate cancer. Further, the specific JAK and STAT proteins, as well as the relevant upstream and downstream mediators appear to differ across the cancer spectrum. The majority of investigations into the biology and role of the JAK/STAT pathway do not necessarily consider this subtlety. This reality challenges the contemporary notion that these survival pathways are homogeneous in various cancers. It is therefore, contemplated herein to identify the unique and specific components critical to the cancer survival phenotype related to the JAK/STAT pathway. For example, the inhibition of JAK2 (via knockdown) has different effects in prostate cancer cells under normal androgen levels, vs. castrate (low), vs. castrate-resistant-like androgen levels (no androgens present) (see, Martinez H., et al., Androgen-Sensitive Microsomal Signaling Networks Couples to the Proliferation and Differentiation of Human Prostate Cancer Cells, Genes & Cancer 2(10) 956-978). It has been noted that "[i]nterestingly, quantifiable differences in cell proliferation were not observed in knock-down cells cultured under conditions of androgen depletion." (Id., at 968) Therefore, since the inhibition of JAK has different effects on prostate cancer cell proliferation, depending on androgen availability, one skilled in the art would not anticipate that JAK2 inhibitors would necessarily have the same effect on androgen-sensitive (under normal androgen levels) and androgen-resistant prostate cancer cells. Further, in a review article by Shodeinde and Barton (Shodeinde A. and B. Barton, Potential Use of STAT5 Inhibitors in Targeted Prostate Cancer Therapy: Future Prospects, OncoTargets and Therapy 3 Jul. 2012), the dual JAK1/JAK2 inhibitor ruxtolitinib failed to show efficacy in a Phase II clinical trial with androgen-independent prostate cancer. As this dual JAK1/JAK2 inhibitor did not work in patients with androgen-independent prostate cancer, it would not be readily expected by one skilled in the art that a JAK2 inhibitor alone would work either. However, by investigating the complex interactions between JAK and STAT components of this signaling pathway it is contemplated that specific inhibition of JAK2, either alone or in combination with one or more anticancer agents, such as radiotherapy, for example, will be effective in treating prostate cancer in a subject.

Further, the JAK/STAT pathway is not being investigated in prostate cancer as a potentially targetable survival pathway for which inhibition, and possibly in conjunction with other lethal insults such as combination therapy may be clinically pragmatic. A number of mCRPC treatments targeting various androgen receptor and non-androgen receptor pathways are in development, but are expected to be limited by the fundamental activation of specific survival pathways in this disease. Targeting JAK/STAT could thus inhibit a fundamental property of the malignant phenotype and open the door to multiple therapies including, for example, combination therapy.

Applicants' results suggest that the specifics of JAK/STAT survival pathway signaling are context and disease specific. The specific JAK and STAT proteins family members, as well as the relevant upstream and downstream mediators appear to differ across the cancer spectrum. The majority of previous investigations into the biology and role of the JAK/STAT pathway do not necessarily consider this subtlety. Applicants' hypothesis, therefore, challenges the notion that these survival pathways are homogeneous in various cancers and seeks to identify the unique and specific components critical to one illustrative cancer, the mCRPC survival phenotype.

Based on the above discussion, Applicants describe several illustrative approaches to determine the JAK/STAT pathway survival mechanisms specific to a particular cancer, prostate cancer. Applicants envision that such approaches can be used in other cancer targets to determine the role of this pathway on cancer survival. Such approaches described herein include:

a) Dissection of the relative impact of JAK1 vs. JAK2 and STAT1 vs. STAT3 on JAK/STAT-dependent tumor survival, and/or b) Validate MCL1 (Myeloid Cell Leukemia sequence 1; Entrez Gene ID for Human: 4170; HGNC ID: 6943; Ensembl ID: ENSG000001433847; OMIM ID: 1595525; UniProtKB ID: Q078203) as a down-stream mediator of JAK/STAT-dependent survival pathways and as a potential additional target for radio/chemosensitization of hormone-resistant prostate cancer.

Using mCRPC as an example, a "successful" cancer in a subject, has survived a myriad of insults that would be expected to be lethal to most cells. Applicants now show that certain cellular survival pathways are upregulated and highly active in mCRPC. It is expected that such cells would be resistant to further lethal insults (for example, chemotherapy and/or radiotherapy) and successful therapy may employ the addition of a survival pathway inhibitor. The survival pathway in such cancers, including those that are chemoresistant and/or radioresistant, is believed to be the JAK/STAT pathway, which may include, for example, the JAK2/STAT1-STAT3 signaling members. Furthermore, it is also believed that the anti-apoptotic protein MCL1 is a downstream mediator of this survival pathway. It is further expected that the JAK/STAT pathway maintains cancer cell survival status and is, therefore, a viable therapeutic target. One approach is to determine JAK/STAT pathway survival mechanisms in a particular cancer. By utilizing a combination of sh/siRNA and chemical approaches with JAK2 specific and broader JAK1/2 inhibitors in genetically related cancer cell lines, for example, CWRR1 (resistant to JAK2 inhibition) and CW22RV1 (sensitive to JAK2 inhibition) in prostate cancer, the relative contributions of JAK1 and JAK2 can be determined as well as the relative contribution of STAT1 versus STAT5 in mediating survival. Further, the role of MCL1 as an effector of the JAK/STAT survival pathway in the particular cancer can also be evaluated.

Figure 1:
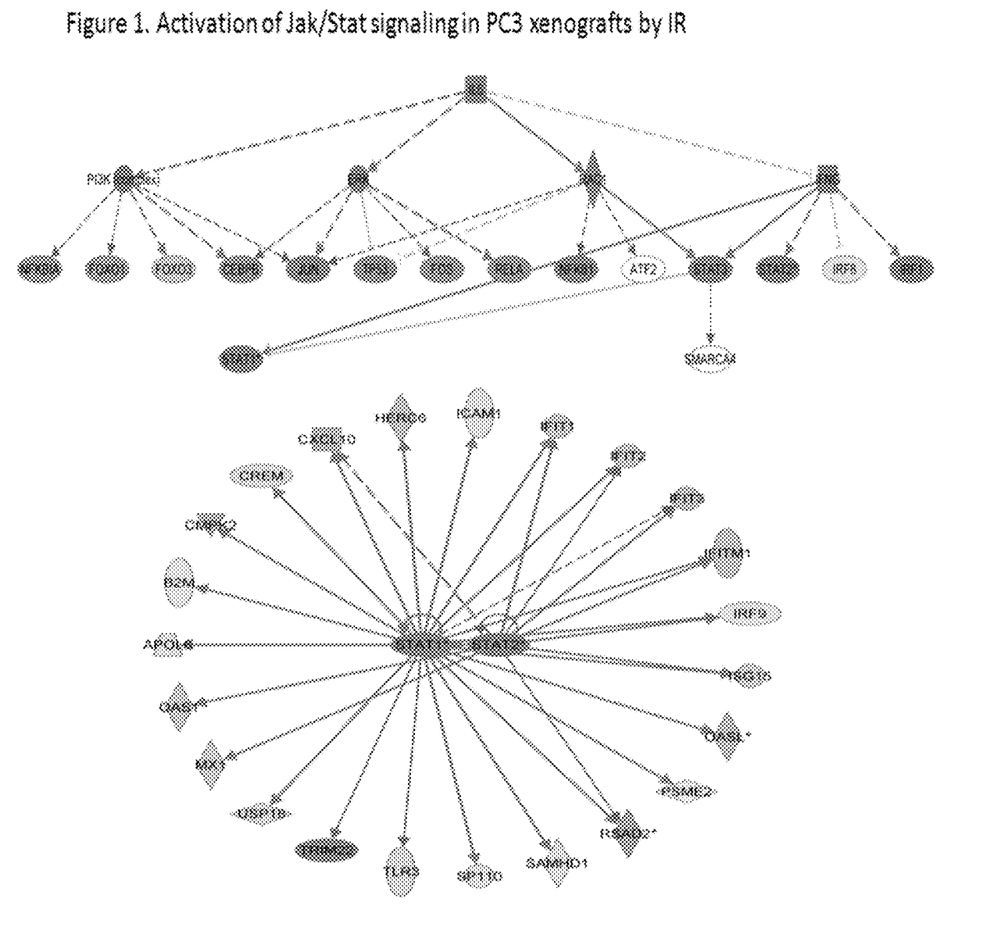
FIG. 1 shows the results of a gene profiling experiment using Affymetrix microarrays on PC3 prostate cancer mouse xenografts following irradiation.
Figure 2:
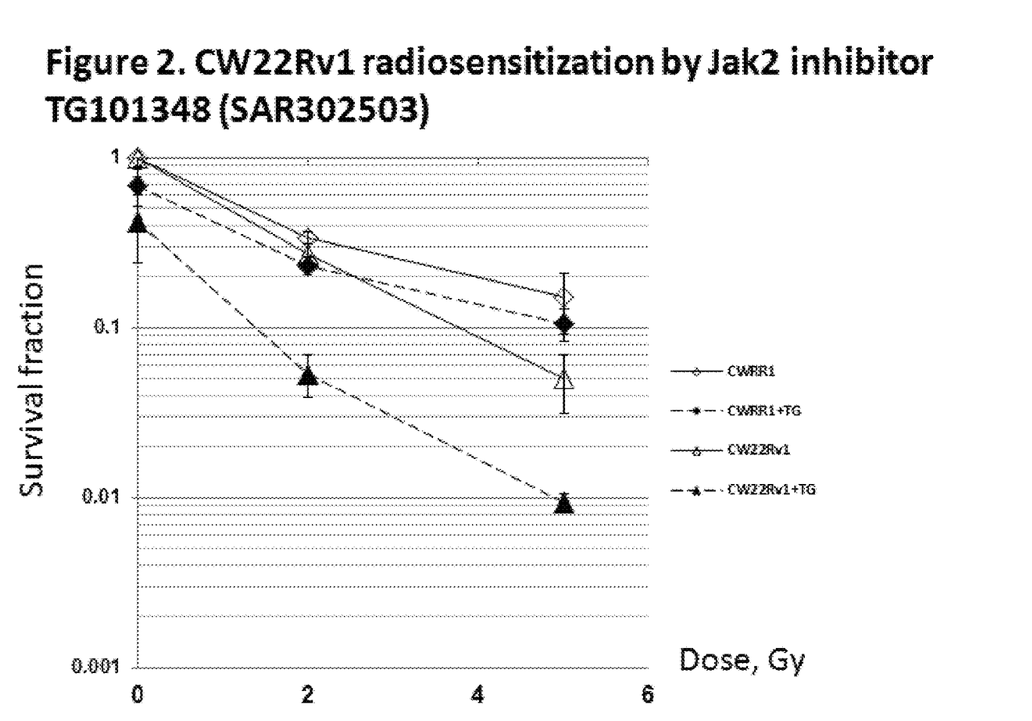
FIG. 2 shows the effect of JAK2 inhibitor SAR302503 in prostate cancer cell lines CWRR1 and CW22Rv1 treated with gamma radiation.

For example, Applicants have now shown that in hormone resistant prostate cancer cells, sensitive to JAK inhibitors, JAK2 inhibitors alone can suppress tumor growth and in combination with ionizing radiation lead to significant suppression of tumor growth (FIGS. 1 and 2). Based on this observation, a JAK2 inhibitor can be used as primary therapy in patients with hormone resistant prostate cancer (localized) and/or treatment of hormone refractory metastatic prostate cancer for cure or palliation in combination with radio isotopes such as summerium and radium 223, which are employed in metastatic hormone refractory cancer.

Another approach is to develop combination therapy that includes JAK inhibitor therapies. For example, it is contemplated that JAK2 inhibition will enhance classic cytotoxic therapy, such as the standard taxanes. Taxanes are produced by the plants of the genus *Taxus* and are classified as diterpenes and widely used as chemotherapy agents including, for example, paclitaxel (Taxol®, Bristol-Meyers Squibb, CAS 33069-62-4) or docetaxel (Taxotere®, Sanofi-Aventis, CAS 114977-28-5). It is also contemplated that combinations of semi-synthetic derivatives of a natural taxoid and a JAK2 inhibitor will also enhance cytotoxic therapy. One such example of a semi-synthetic derivative of taxoid is cabazitaxel (Jevtana®, Sanofi-Aventis, CAS 183133-96-2), and an example of a JAK2 inhibitor is SAR302503 (Sanofi-Aventis, CAS 936091-26-8). Other JAK2 inhibitors include, for example, CYT387 (YM Biosciences Inc., CAS 1056634-68-4), SB1518 [pacritinib, S*BIO Pte Ltd. (Singapore, Singapore), CAS 937272-79-2], CEP701 (lestaurtinib, Cephalon, CAS 111358-88-4), and LY2784544 (Eli Lilly and Company, CAS 1229236-86-5). The dose-limiting toxicity of such a combination is expected to be myelosuppression. Other combinations of JAK2 inhibitor therapy for the treatment of cancer contemplated herein, include radiotherapy, and other cancer specific agents, such as an androgen receptor inhibitor or mediator. Illustrative androgen receptor inhibitors include, for example, a steroidal antiandrogen (for example, cyperterone, CAS 2098-66-0); a non-steroidal antiandrogen (for example, flutamide, Eulexin®, Schering-Plough, CAS 13311-84-7); nilutamide (Nilandron®, CAS 63612-50-0); enzalutamide (Xtandi®, Medivation, CAS 915087-33-1); bicalutamide (Casodex®, AstraZeneca, CAS 90357-06-5); a peptide antiandrogen; a small molecule antiandrogen (for example, RU58642 (Roussel-Uclaf SA, CAS 143782-63-2); LG120907 and LG105 (Ligand Pharmaceuticals); RD162 (Medivation, CAS 915087-27-3); BMS-641988 (Bristol-Meyers Squibb, CAS 573738-99-5); and CH5137291 (Chugai Pharmaceutical Co. Ltd., CAS 104344603904)); a natural antiandrogen (for example, ataric acid (CAS 4707-47-5) and N-butylbensensulfonamide (CAS 3622-84-2); a selective androgen receptor modulator for example, enobosarm (Ostarine®, Merck & Company, CAS 841205-47-8); BMS-564,929 (Bristol-Meyer Squibb, CAS 627530-84-1); LGD-4033 (CAS 115910-22-4); AC-262,356 (Acadia Pharmaceuticals); LGD-3303 (Ganolix Lifescience Co., Ltd., 9-chloro-2-ethyl-1-methyl-3-(2,2,2-trifluoroethyl)-3H-pyrrolo [3,2-f] quinolin-7(6H)-one; S-40503, Kaken Pharmaceuticals, 2-[4-(dimethylamino)-6-nitro-1,2,3,4-tetrahydroquinolin-2-yl]-2-methylpropan-1-ol); andarine (GTx-007, S-4, GTX, Inc., CAS 401900-40-1); and S-23 (GTX, Inc., (2S)—N-(4-cyano-3-trifluoromethylphenyl)-3-(3-fluoro-4-chlorophenoxy)-2-hydroxy-2-methyl-propanamide)); or those described in U.S. Patent Appln. No. 2009/0304663.

Other cancer specific agents or chemotherapeutic agents that may be used in combination with JAK inhibitor therapy include, for example: alkylating agents such as nitrogen mustards such as mechlorethamine ($HN_2$), cyclophosphamide, ifosfamide, melphalan (L-sarcolysin) and chlorambucil; ethylenimines and methylmelamines such as hexamethylmelamine, thiotepa; alkyl sulphonates such as busulfan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin); natural products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; biological response modifiers such as interferon alphenomes; other agents such as platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MTH); adrenocortical suppressant such as mitotane (o,p'-DDD) and aminoglutethimide; taxol analogues/derivatives; hormone agonists/antagonists such as flutamide and tamoxifen; and GnRH and analogues thereof.

Applicants further believe that activation of the JAK/STAT pathway is a survival pathway for a proportion of cancers surviving in a subject and that targeting this pathway will result in a toxic insult to the cancer, leading to, for example, inhibiting the growth or proliferation of the cancer, inducing the killing of the cancer, and/or inhibiting or reversing the development or progression of the cancer in a subject. By specifically addressing one or more of the following areas in a collaborative, integrated and multi-disciplinary project, it is contemplated that novel therapies can be developed for this lethal and burdensome disease, and may also provide therapeutic insight into adaptive mechanisms that can be ascertained as operative in malignancies such as tumors and cancer: a) dissect the components of the JAK/STAT pathway that are most relevant to the cancer survival phenotype, b) develop biomarkers for identifying the cancers with this pathway activated and which are thus susceptible to its targeting, c) develop the clinical science of introducing JAK inhibitors to the treatment of the cancer in a subject, and d) develop inhibitor(s) of the JAK/STAT pathway, including selective inhibitors to the most relevant components of the JAK/STAT pathway responsible for the survival phenotype.

It is further believed that the specifics of JAK/STAT survival pathway signaling are context and disease specific. An observation made in breast cancer that radioresistant aggressive tumors express a transcriptomic signature closely related to interferon signaling, which makes these cells highly resistant to a variety of therapies and enhances their metastatic propensity. Of note, this signature is comprised of genes activated by JAK1/JAK2/STAT1/STAT3 signaling. This activated JAK/STAT pathways are common in multiple clinical and preclinical tumor models, and have been linked to poor prognosis. In prostate cancer, for example, high expression of both pJAK1 and pSTAT3 have been associated with decreased recurrence free survival following both definitive therapy for localized disease as well as androgen deprivation. Furthermore anti-sense inhibition of STAT3 has been suggested to enhance apoptosis in prostate cancer cell lines.

Surprisingly and unexpectedly, Applicants' results show that the components mediating the survival pathway in prostate cancer are JAK1, JAK2, STAT1 and STAT3. As such and as described more fully below, Applicants' approach includes pharmacological and h/siRNA-based approaches combined with growth/survival assays, biochemical analysis and whole-genome expressional profiling to estimate the relative contribution of JAK1, JAK2, STAT1 and STAT3 on growth and radio/chemoresistance of prostate cancer cells.

It is also important to elucidate the specific mediators of the survival phenotype of prostate cancer cells with an activated JAK/STAT pathway, since these may provide insight into effective pathway targeting. Applicants have shown that the survival phenotype of castrate resistant cell lines CWRR1 and CW22Rv1 is dependent on MCL1, which is both a STAT1 as well as a STAT3 regulated gene. MCL1 is also an apoptosis inhibitor commonly amplified in various cancers, including prostate cancer. Applicants conclude, therefore, that MCL1 is a mediator of the JAK/STAT dependent survival phenotype and provides not only mechanistic insight, but an additional therapeutic target to prostate cancer.

The overarching hypothesis addressed is that JAK/STAT signaling is needed for maintaining cancer cell survival in a subset of cancers, including, for example, late stage castrate resistant prostate cancers, particularly in the context of additional toxic insults, and is therefore a therapeutic target. To address this hypothesis in mCRPC, for example, a multi-prong, interdisciplinary, and highly interactive approach was taken with three basic approaches. The first approach identified and elucidated the specifics of the JAK/STAT pathway relevant for the survival phenotype in mCRPC utilizing a combination of genetic and chemical approaches. The second approach develops the clinical science necessary for introducing JAK inhibitors into the therapeutic armamentarium under the hypothesis that effective targeting may include combination strategies. These specific approaches may be carried out simultaneously, but each can and will be modified on the basis of emerging data from the other specific aims. Further, within the first approach, there were 2 subaims: 1) to dissect the relative impact of JAK1 vs. JAK2 and STAT1 vs. STAT3 on JAK/STAT-dependent tumor survival, and 2) to validate MCL1 as a down-stream mediator of JAK/STAT-dependent survival pathways and as a potential additional target for radio/chemosensitization of hormone-resistant prostate cancer; and within the second approach there were three subaims: 1) to conduct in vivo xenograft studies of SAR302503 in combination with various standard prostate cancer treatments, and 2) to conduct a human phase 1 clinical trial of SAR302503 and cabazitaxel in patients with castrate resistant prostate cancer.

The term "subject" refers to any organism classified as a mammal, including mice, rats, guinea pigs, rabbits, dogs, cats, cows, horses, monkeys, and other mammals. In one preferred embodiment, the subjects are humans.

As used herein, the term "cancer" refers to a class of diseases of mammals characterized by uncontrolled cellular growth. The term "cancer" is used interchangeably with the terms "tumor," "solid tumor," "malignancy," "hyperproliferation" and "neoplasm." Cancer includes all types of hyperproliferative growth, hyperplasic growth, neoplastic growth, cancerous growth or oncogenic processes, metastatic tissues or malignantly transformed cells, tissues, or organs, irrespective of histopathologic type or stage of invasiveness. Illustrative examples include, lung, prostate, head and neck, breast and colorectal cancer, melanomas and gliomas (such as a high grade glioma, including glioblastoma multiforme (GBM), the most common and deadliest of malignant primary brain tumors in adult humans).

As used herein, the phrase "solid tumor" includes, for example, lung cancer, head and neck cancer, brain cancer, oral cancer, colorectal cancer, breast cancer, prostate cancer, pancreatic cancer, and liver cancer. Other types of solid tumors are named for the particular cells that form them, for example, sarcomas formed from connective tissue cells (for example, bone cartilage, fat), carcinomas formed from epithelial tissue cells (for example, breast, colon, pancreas) and lymphomas formed from lymphatic tissue cells (for example, lymph nodes, spleen, thymus). Treatment of all types of solid tumors regardless of naming convention is within the scope of this invention.

JAK (Janus Kinase) refers to a family of intracellular, nonreceptor tyrosine kinases. JAK may include four family members, Janus 1 (JAK1), Janus 2 (JAK2), Janus 3 (JAK3), and Tyrosine kinase 2 (Tyk2).

STAT (Signal Transducer and Activator of Transcription) plays a role in regulating cell growth, survival and differentiation and the family includes STAT1, STAT2, STAT 3, STAT4, STAT5 (STAT5a and STAT5b), and STAT6.

The phrase "JAK/STAT pathway inhibitor," as used herein, refers to an inhibitor that provides inhibition of the pathway to an extent that can be measured by conventional biochemical techniques.

Methods and assays for determining the level of JAK inhibition, and for determining whether and to what extent an agent inhibits JAK, are described in, for example, Babon J J, Murphy J M, In vitro JAK kinase activity and inhibition assays, Methods Mol Biol. 2013; 967:39-55.

Without being bound by theory, Applicants envision that the JAK inhibitor will be therapeutically useful in a subject with a cancer having an activated JAK. The activity of JAK and its family members can be measured directly by kinase assay, or indirectly by staining with commercially available antibodies (including, for example, antibody for total Jak2 sc-294, and antibody for activated (phosphorylated) Jak2 c-21870, Santa Cruz Biotechnology, CA), as is well known to a person skilled in the art.

Without being bound by theory, Applicants appreciate that JAK inhibitors may not work in a subject with a cancer that express little or no levels of MCL1. Thus, a typical subject is one with cancer that expresses elevated or high levels of MCL1 as compared to a normal non-disease state subject. Based on transcriptional data (see Oncomine: https://www.oncomine.org/resource/main.html) expressional levels of MCL1 mRNA are increased in prostate carcinomas relative to normal prostate tissues at 20-30% in average (see Taylor B S et al., Cancer Cell, 2010, *Integrative genomic profiling of human prostate cancer.* Cancer Cell. 2010 Jul. 13; 18(1): 11-22; Yu Y P, Landsittel D, Jing L, Nelson J, Ren B, Liu L, McDonald C, Thomas R, Dhir R, Finkelstein S, Michalopoulos G, Becich M, Luo J H. *Gene expression alterations in prostate cancer predicting tumor aggression and preceding development of malignancy.* J Clin Oncol. 2004 Jul. 15; 22(14):2790-9.). As more objective measure, increase in the copy numbers of MCL1 gene can be considered, where any significant increase of copy numbers>than 2 per cell can be considered as elevated (see The Cancer Genome Atlas—Prostate Adenocarcinoma DNA Copy Number Data, http://tcga-data.nci.nih.gov/tcga/).

It is also contemplated that the JAK inhibitor may be, for example, a molecule that binds to the active or inactive conformation of the kinase ATP pocket or a non-ATP competitive kinase inhibitor, and can be a small molecule, a polynucleotide, or encoded by a polynucleotide, for example. Polynucleotides may be administered by any effective method known in the art, for example, parenterally (e.g., intravenously, subcutaneously, intramuscularly) or by oral, nasal or other means that permit the oligonucleotides to access and circulate in the subject's bloodstream. Polynucleotides administered systemically may be given in addition to locally administered polynucleotides, but also have utility in the absence of local administration. A dosage in the range of from about 0.1 to about 10 grams per administration to an adult human will likely be effective for this purpose. The polynucleotide may also be administered as a suitable genetic construct or as nanoparticle (as is described in Costa P M et al., Mol Ther Nucleic Acids. 2013 Jun. 18; 2:e100) and delivered to the subject where it is expressed. Typically, the polynucleotide in the genetic construct is operatively linked to a promoter that can express the compound in the cell. The genetic constructs can be prepared using methods well known in the art, for example, Gil M, Seshadri M, Komorowski M P, Abrams S I, Kozbor D., Targeting CXCL12/CXCR4 signaling with oncolytic virotherapy disrupts tumor vasculature and inhibits breast cancer metastases, Proc Natl Acad Sci USA. 2013 Apr. 2; 110(14):E1291-300.

The present disclosure also includes the use of an inhibitor of JAK or polynucleotide which encodes an inhibitor of JAK in the preparation of a medicament for the treatment of cancer, including prostate cancer, and in a subject, who may also be administered a further anti-cancer agent. The subject may have been administered the anti-cancer agent previously, or is administered the anti-cancer agent simultaneously with the medicament, or is administered the anti-cancer agent after the medicament.

The phrases "selective JAK/STAT pathway inhibitor," or "selective JAK inhibitor," or "selective STAT inhibitor," refer to an inhibitor that inhibits a particular member of the JAK or STAT family a greater extent than that of another member of the family. For example, a selective JAK inhibitor may include: 1) an inhibitor that selectively inhibits JAK1 but not JAK2, JAK3, or Tyk2; or 2) an inhibitor that selectively inhibits JAK2 but not JAK1, JAK3, or Tyk2. A selective STAT inhibitor may include, for example: 1) an inhibitor that selectively inhibits STAT 1, but not STAT2, STAT 3, STAT4, STAT5 (STAT5a and STAT5b), and STAT6; or 2) an inhibitor that selectively inhibits STAT 2, but not STAT1, STAT 3, STAT4, STAT5 (STAT5a and STAT5b), and STAT6. Selective inhibition refers to inhibition of the particular family member that is about 2-fold to about 10-fold greater than that of the other family members (that is based on differences in the constants of inhibition).

Suppression of a gene refers to the absence of expression of a gene or a decrease in expression of a gene as compared to the activity of an untreated gene. Suppression of a gene may be determined by detecting the presence or absence of expression of a gene or by measuring a decrease of expression of a gene by any means known in the art including, for example, detecting a decrease in the level of the final gene product, such as a protein, or detecting a decreased level of a precursor, such as mRNA, from which gene expression levels may be inferred when compared to normal gene activity, such as a negative (untreated) control. Any molecular biological assay to detect mRNA or an immunoassay to detect a protein known in the art can be used. A molecular biological assay may include, for example, polymerase chain reaction (PCR), Northern blot, Dot blot, or an analysis method with microarray or macroarray. An immunological assay includes, for example, ELISA (enzyme-linked immunosorbent assay) with a microtiter plate, radioimmunoassay (RIA), a fluorescence antibody technique, Western blotting, or an immune structure dyeing method. Suppression of a gene may also be inferred biologically in vivo, in situ, and/or in vitro, by the suppression of growth or proliferation of a tumor or cancer cell, cell death of a tumor or cancer cell, and/or the sensitization of a tumor or cancer cell to chemotherapy and/or radiotherapy. Illustratively, a therapeutically effective amount of gene suppression in a subject results in the suppression of growth or proliferation of a tumor or cancer cell, cell death of the tumor or cancer cell, and/or the sensitization of the tumor or cancer cell to chemotherapy and/or radiotherapy. As each subject is different and each cancer is different, the amount of gene suppression to achieve a therapeutically effective amount of gene suppression may be determined by a trained professional skilled in the area on a case-by-case basis. Illustratively, a therapeutically effective amount of gene suppression may include, for example, less than or equal to about 95% of normal gene activity, or less than or equal to about 90% of normal gene activity, or less than or equal to about 85% of normal gene activity, or less than or equal to about 80% of normal gene activity, or less than or equal to about 75% of normal gene activity, or less than or equal to about 65% of normal gene activity, or less than or equal to about 50% of normal gene activity, or less than or equal to about 35% of normal gene activity, or less than or equal to about 25% of normal gene activity, or less than or equal to about 15% of normal gene activity, or less than or equal to about 10% of normal gene activity, or less than or equal to about 7.5% of normal gene activity, or less than or equal to about 5% of normal gene activity, or less than or equal to about 2.5% of normal gene activity, or less than or equal to about 1% of normal gene activity, or less than or equal to about 0% of normal gene activity.

Suppression of identified genes individually or in combination with ionizing radiation and/or any chemotherapeutic agents may improve the outcome of patients treated with the ionizing radiation or any chemotherapy agent or any treatment designed to improve outcome of the cancer patients (like JAK1/JAK2 inhibitors) if such treatment is combined with the suppression of any of these genes or their combination.

Radiotherapy is based on ionizing radiation delivered to a target area that results in death of reproductive tumor cells. Some examples of radiotherapy include the radiation of cesium, palladium, iridium, iodine, or cobalt radiotherapy which is usually delivered as ionizing radiation from a linear accelerator or an isotopic source such as a cobalt source. Also variations on linear accelerators are Cyberkine and Tomotherapy. Particle radiotherapy from cyclotrons such as Protons or Carbon nuclei may be employed. Also radioisotopes delivered systemically such as p32 or radium 223 may be used. The external radiotherapy may be systemic radiation in the form of sterotacktic radiotherapy total nodal radiotherapy or whole body radiotherapy but is more likely focused to a particular site, such as the location of the tumor or the solid cancer tissues (for example, abdomen, lung, liver, lymph nodes, head, etc.). The radiation dosage regimen is generally defined in terms of Gray or Sieverts time and fractionation, and must be carefully defined by the radiation oncologist. The amount of radiation a subject receives will depend on various considerations. The two important considerations are the location of the tumor in relation to other critical structures or organs of the body, and the extent to which the tumor has spread. One illustrative course of treatment for a subject undergoing radiation therapy is a treatment schedule over a 5 to 8 week period, with a total dose of 50 to 80 Gray (Gy) administered to the subject in a single daily fraction of 1.8 to 2.0 Gy, 5 days a week. A Gy is an abbreviation for Gray and refers to 100 rad of dose.

Radiotherapy can also include implanting radioactive seeds inside or next to an site designated for radiotherapy and is termed brachytherapy (or internal radiotherapy, endocurietherapy or sealed source therapy). For prostate cancer, there are currently two types of brachytherapy: permanent and temporary. In permanent brachytherapy, radioactive (iodine-125 or palladium-103) seeds are implanted into the prostate gland using an ultrasound for guidance. Illustratively, about 40 to 100 seeds are implanted and the number and placement are generally determined by a computer-generated treatment plan known in the art specific for each subject. Temporary brachytherapy uses a hollow sources placed into the prostate gland that is filled with radioactive material (iridium-192) for about 5 to about 15 minutes, for example. Following treatment, the needle and radioactive material are removed. This procedure is repeated two to three times over a course of several days.

Radiotherapy can also include radiation delivered by external beam radiation therapy (EBRT), including, for example, a linear accelerator (a type of high-powered X-ray machine that produces very powerful photons that penetrate deep into the body); proton beam therapy where photons are derived from a radioactive source such as iridium-192, caesium-137, radium-226 (no longer used clinically), or cobalt-60; Hadron therapy; multi-leaf collimator (MLC); and intensity modulated radiation therapy (IMRT). During this type of therapy, a brief exposure to the radiation is given for a duration of several minutes, and treatment is typically given once per day, 5 days per week, for about 5 to 8 weeks. No radiation remains in the subject after treatment. There are several ways to deliver EBRT, including, for example, three-dimensional conformal radiation therapy where the beam intensity of each beam is determined by the shape of the tumor. Illustrative dosages used for photon based radiation is measured in Gy, and in an otherwise healthy subject (that is, little or no other disease states present such as high blood pressure, infection, diabetes, etc.) for a solid epithelial tumor ranges from about 60 to about 80 Gy, and for a lymphoma ranges from about 20 to about 40 Gy. Illustrative preventative (adjuvant) doses are typically given at about 45 to about 60 Gy in about 1.8 to about 2 Gy fractions for breast, head, and neck cancers.

When radiation therapy is a local modality, radiation therapy as a single course of therapy is unlikely to provide a cure for those tumors that have metastasized distantly outside the zone of treatment. Thus, the use of radiation therapy with other modality regimens, including chemotherapy, have important beneficial effects for the treatment of metastasized cancers.

Radiation therapy has also been combined temporally with chemotherapy to improve the outcome of treatment. There are various terms to describe the temporal relationship of administering radiation therapy and chemotherapy, and the following examples are illustrative treatment regimens and are generally known by those skilled in the art and are provided for illustration only and are not intended to limit the use of other combinations. "Sequential" radiation therapy and chemotherapy refers to the administration of chemotherapy and radiation therapy separately in time in order to allow the separate administration of either chemotherapy or radiation therapy. "Concomitant" radiation therapy and chemotherapy refers to the administration of chemotherapy and radiation therapy on the same day. Finally, "alternating" radiation therapy and chemotherapy refers to the administration of radiation therapy on the days in which chemotherapy would not have been administered if it was given alone.

It should be noted that other therapeutically effective doses of radiotherapy can be determined by a radiation oncologist skilled in the art and can be based on, for example, whether the subject is receiving chemotherapy, if the radiation is given before or after surgery, the type and/or stage of cancer, the location of the tumor, and the age, weight and general health of the subject.

Based on the functional groups, we also contemplate that suppression of the chemokine signaling, or suppression of negative regulators of interferon response, or suppression of protein degradation or mitochondria-related anti-apoptotic molecules or anti-viral proteins or extracellular matrix proteins (ECM) alone or in combination with ionizing radiation or any chemotherapy drug or any treatment designed to improve outcome of the cancer patients will improve cancer treatment. This is based on the functional associations between detected targets. DHX58 (also known as LGP2) is known as an apical suppressor of RNA dependent activation of the Type I interferons alpha and beta. IFITM1 and OASL are known anti-viral proteins. USP18 and HERC5 are enzymes involved in protein ISGylation/de-ISGylation, known to protect proteins from ubiquitin-dependent degradation in proteosome complex, while PSMB9 and PSMB10 are proteasome subunits. EPSTL1, LGALS3P and TAGLN are involved in the structure and functional regulation of ECM. CXCL9 and CCL2 are chemokines with multiple functions including growth-promoting functions for tumor cells.

As used herein, the term "chemoresistant" refers to a tumor or cancer cell that shows little or no significant detectable therapeutic response to an agent used in chemotherapy.

As used herein, the term "radioresistant" refers to a tumor or cancer cell that shows little or no significant detectable therapeutic response to an agent used in radiotherapy such as ionizing radiation.

As used herein, the term "chemosensitive" refers to a tumor or cancer cell that shows a detectable therapeutic response to an agent used in chemotherapy.

As used herein, the term "radiosensitive" refers to a tumor or cancer cell that shows a detectable therapeutic response to an agent used in radiotherapy.

As used herein, the phrases "chemotherapeutic agent," "cytotoxic agent," "anticancer agent," and "antitumor agent" are used interchangeably and refer to an agent that has the effect of inhibiting the growth or proliferation, or inducing the killing, of a tumor or cancer cell. The chemotherapeutic agent may inhibit or reverse the development or progression of a tumor or cancer, such as for example, a solid tumor.

As used herein, the term "chemotherapy" refers to administration of at least one chemotherapeutic agent to a subject having a tumor or cancer.

As used herein, the term "radiotherapy" refers to administration of at least one "radiotherapeutic agent" to a subject having a tumor or cancer and refers to any manner of treatment of a tumor or cancer with a radiotherapeutic agent. A radiotherapeutic agent includes, for example, ionizing radiation including, for example, external beam radiotherapy, stereotactic radiotherapy, virtual simulation, 3-dimensional conformal radiotherapy, intensity-modulated radiotherapy, ionizing particle therapy and radioisotope therapy.

The term "taxoid," as used herein, refers to a class of derivatives from taxol, which were developed for their anti-cancer properties. Taxoids are similar to taxanes. Taxoids may include taxotere.

The term "paclitaxel," as used herein, refers to a mitotic inhibitor used in cancer chemotherapy. It was discovered in a US National Cancer Institute program at the Research Triangle Institute in 1967 when Monroe E. Wall and Mansukh C. Wani isolated it from the bark of the Pacific yew tree, *Taxus brevifolia* and named it taxol. Later it was discovered that endophytic fungi in the bark synthesize paclitaxel.

Paclitaxel may be used to treat patients with lung, ovarian, breast, head and neck cancer, and advanced forms of Kaposi's sarcoma. Paclitaxel may be also used for the prevention of restenosis.

Paclitaxel stabilizes microtubules and, as a result, interferes with the normal breakdown of microtubules during cell division. Together with docetaxel, it forms the drug category of the taxanes.

The term "Docetaxel," as used herein, refers to a clinically well-established anti-mitotic chemotherapy medication that works by interfering with cell division. Docetaxel is as generic or under the trade name Taxotere or Docecad. Docetaxel is approved by the FDA for treatment of locally advanced or metastatic breast cancer, head and neck cancer, gastric cancer, hormone-refractory prostate cancer and non small-cell lung cancer. Docetaxel can be used as a single agent or in combination with other chemotherapeutic drugs as indicated depending on specific cancer type and stage.

Docetaxel is a member of the taxane drug class, which also includes the chemotherapeutic medication paclitaxel. Although docetaxel remains twice as potent as paclitaxel (due to docetaxel's effect on the centrosome of the mitotic spindle), the two taxanes have been observed to have comparable efficacy.

The term "cabazitaxel," previously "XRP-6258," or trade name "Jevtana," as used herein, refers to a semi-synthetic derivative of a natural taxoid. It was developed by Sanofi-Aventis and was approved by the U.S. Food and Drug Administration (FDA) for the treatment of hormone-refractory prostate cancer on Jun. 17, 2010. It is a microtubule inhibitor, and the fourth taxane to be approved as a cancer therapy.

Cabazitaxel in combination with prednisone is a treatment option for hormone-refractory prostate cancer following docetaxel-based treatment.

The term "antiandrogen" or "androgen antagonists," as used herein, refers to any compound or substance which can prevent androgens from expressing their biological effects on responsive tissues. Antiandrogens may alter the androgen pathway by blocking the appropriate receptors, competing for binding sites on the cell's surface, or affecting androgen production. Antiandrogens can be prescribed to treat an array of diseases and disorders. In men, antiandrogens are most frequently used to treat prostate cancer. In women, antiandrogens are used to decrease levels of male hormones causing symptoms of hyperandrogenism. Antiandrogens present in the environment have become a topic of concern. Many industrial chemicals, pesticides and insecticides exhibit antiandrogenic effects. Certain plant species have also been found to produce antiandrogens. Environmental antiandrogens can have harmful effects on reproductive organ development in fetuses exposed in utero as well as their offspring.

The phrase "combination therapy" (or "co-therapy") embraces the administration of an agent used in JAK/STAT pathway inhibition and one or more of anticancer agents such as a chemotherapeutic agent and/or radiation therapy, as part of a specific treatment regimen intended to provide a beneficial effect from the co-action of the JAK/STAT pathway inhibitor and the other agent. The beneficial effect of the combination may include, but is not limited to, pharmacokinetic or pharmacodynamic co-action resulting from the combination. Administration of the combination typically is carried out over a defined time period (usually minutes, hours, days or weeks depending upon the combination selected). "Combination therapy" generally is not intended to encompass the administration of an agent as part of separate monotherapy regimens that incidentally and arbitrarily result in the combinations of the present invention. "Combination therapy" is intended to embrace administration of the agents in a sequential manner, that is, wherein the agents are administered at different times, as well as administration of the agents in a substantially simultaneous manner. Substantially simultaneous administration can be accomplished, for example, by administering to the subject concurrently with radiation therapy a single capsule having a fixed ratio of each therapeutic agent or in multiple, single capsules for each therapeutic agent. Sequential or substantially simultaneous administration of each therapeutic agent can be effected by any appropriate route including, but not limited to, oral routes, intravenous routes, intramuscular routes, and direct absorption through mucous membrane tissues. The therapeutic agents, if more than one, can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the agents are administered is not narrowly critical although radiation therapy typically will follow the administration of the JAK2 inhibitor. "Combination therapy" can also embrace the administration of the agents as described above in further combination with other biologically active ingredients (such as, but not limited to, an antineoplastic agent) and non-drug therapies (such as, but not limited to, surgery). The radiation treatment of the combination may be conducted at any suitable time so long as a beneficial effect from the co-action of the combination of the agents is achieved. For example, in appropriate cases, the beneficial effect is still achieved even when the radiation treatment is temporally removed from the administration of the other agent, perhaps by days or even weeks.

An illustrative antineoplastic agent or chemotherapeutic agent may include, for example, a standard taxane. Taxanes are produced by the plants of the genus *Taxus* and are classified as diterpenes and widely uses as chemotherapy agents including, for example, paclitaxel, (Taxol®, Bristol-Meyers Squibb, CAS 33069-62-4) and docetaxel (Taxotere®, Sanofi-Aventis, CAS 114977-28-5). Other chemotherapeutic agent may include semi-synthetic derivatives of a natural taxoid such as cabazitaxel (Jevtana®, Sanofi-Aventis, CAS 183133-96-2). Other chemotherapeutic agent may also include an androgen receptor inhibitor or mediator. Illustrative androgen receptor inhibitors may include, a steroidal antiandrogen (for example, cyperterone, CAS 2098-66-0); a non-steroidal antiandrogen (for example, flutamide, Eulexin®, Schering-Plough, CAS 13311-84-7); nilutamide (Nilandron®, CAS 63612-50-0); enzalutamide (Xtandi®, Medivation®, CAS 915087-33-1); bicalutamide (Casodex, AstraZeneca, CAS 90357-06-5); a peptide antiandrogen; a small molecule antiandrogen (for example, RU58642 (Roussel-Uclaf SA, CAS 143782-63-2); LG120907 and LG105 (Ligand Pharmaceuticals); RD162 (Medivation, CAS 915087-27-3); BMS-641988 (Bristol-Meyers Squibb, CAS 573738-99-5); and CH5137291 (Chugai Pharmaceutical Co. Ltd., CAS 104344603904)); a natural antiandrogen (for example, ataric acid (CAS 4707-47-5) and N-butylbensensulfonamide (CAS 3622-84-2); a selective androgen receptor modulator (for example, enobosarm (Ostarine®, Merck & Company, CAS 841205-47-8); BMS-564,929 (Bristol-Meyer Squibb, CAS 627530-84-1); LGD-4033 (CAS 115910-22-4); AC-262,356 (Acadia Pharmaceuticals); LGD-3303 (Ganolix Lifescience Co., Ltd., 9-chloro-2-ethyl-1-methyl-3-(2,2,2-trifluoroethyl)-3H-pyrrolo [3,2-f] quinolin-7(6H)-one; S-40503, Kaken Pharmaceuticals, 2-[4-(dimethylamino)-6-nitro-1,2,3,4-tetrahydroquinolin-2-yl]-2-methylpropan-1-ol); andarine (GTx-007, S-4, GTX, Inc., CAS 401900-40-1); and S-23 (GTX, Inc., (2S)—N-(4-cyano-3-trifluoromethylphenyl)-3-(3-fluoro-4-chlorophenoxy)-2-hydroxy-2-methyl-propanamide)); or those described in U.S. Patent Appln. No. 2009/0304663. Other neoplastic agents or chemotherapeutic agents that can be used may include, for example: alkylating agents such as nitrogen mustards such as mechlorethamine ($HN_2$), cyclophosphamide, ifosfamide, melphalan (L-sarcolysin) and chlorambucil; ethylenimines and methylmelamines such as hexamethylmelamine, thiotepa; alkyl sulphonates such as busulfan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin); natural products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; biological response modifiers such as interferon alphenomes; other agents such as platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MTH); adrenocortical suppressant such as mitotane (o,p'-DDD) and aminoglutethimide; taxol analogues/derivatives; hormone agonists/antagonists such as flutamide and tamoxifen; and GnRH and analogues thereof. Examples of other chemotherapeutic can be found in Cancer Principles and Practice of Oncology by V. T. Devita and S. Hellman (editors), 6.sup.th edition (Feb. 15, 2001), Lippincott Williams & Wilkins Publishers.

Compositions herein may be formulated for oral, rectal, nasal, topical (including buccal and sublingual), transdermal, vaginal, injection/injectable, and/or parental (including subcutaneous, intramuscular, intravenous, and intradermal) administration. Other suitable administration routes are incorporated herein. The compositions may be presented conveniently in unit dosage forms and may be prepared by any methods known in the pharmaceutical arts. Examples of suitable drug formulations and/or forms are discussed in, for example, Hoover, John E. Remington's Pharmaceutical Sciences, Mack Publishing Co., Easton, Pa.; 18.sup.th edition (1995); and Liberman, H. A. and Lachman, L. Eds., Pharmaceutical Dosage Forms, Marcel Decker, New York, N.Y., 1980. Illustrative methods may include the step of bringing one or more active ingredients into association with a carrier that constitutes one or more accessory ingredients. In general, the compositions may be prepared by bringing into association uniformly and intimately one or more active ingredients with liquid carriers or finely divided solid carriers or both, and then, if necessary, shaping the product.

Pharmaceutical formulations may include those suitable for oral, intramuscular, rectal, nasal, topical (including buccal and sub-lingual), vaginal or parenteral (including intramuscular, subcutaneous and intravenous) administration or in a form suitable for administration by inhalation or insufflation. One or more of the compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

A salt may be a pharmaceutically suitable (i.e., pharmaceutically acceptable) salt including, but not limited to, acid addition salts formed by mixing a solution of the instant compound with a solution of a pharmaceutically acceptable acid. A pharmaceutically acceptable acid may be, for example, hydrochloric acid, methanesulphonic acid, fumaric acid, maleic acid, succinic acid, acetic acid, benzoic acid, oxalic acid, citric acid, tartaric acid, carbonic acid or phosphoric acid.

Suitable pharmaceutically-acceptable salts may further include, but are not limited to salts of pharmaceutically-acceptable inorganic acids, including, for example, sulfuric, phosphoric, nitric, carbonic, boric, sulfamic, and hydrobromic acids, or salts of pharmaceutically-acceptable organic acids such propionic, butyric, maleic, hydroxymaleic, lactic, mucic, gluconic, benzoic, succinic, phenylacetic, toluenesulfonic, benzenesulfonic, salicyclic sulfanilic, aspartic, glutamic, edetic, stearic, palmitic, oleic, lauric, pantothenic, tannic, ascorbic, and valeric acids.

Various pharmaceutically acceptable salts may include, for example, the list of FDA-approved commercially marketed salts including acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate, and triethiodide.

A hydrate may be a pharmaceutically suitable (i.e., pharmaceutically acceptable) hydrate that is a compound formed by the addition of water or its elements to a host molecule (for example, the free form version of the compound) including, but not limited to, monohydrates, dihydrates, etc. A solvate may be a pharmaceutically suitable (i.e., pharmaceutically acceptable) solvate, whereby solvation is an interaction of a solute with a solvent which leads to stabilization of the solute species in a solution, and whereby the solvated state is an ion in a solution complexed by solvent molecules. Solvates and hydrates may also be referred to as "analogues."

A prodrug may be a compound that is pharmacologically inert but is converted by enzyme or chemical action to an active form of the drug (i.e., an active pharmaceutical ingredient) at or near the predetermined target site. In other words, prodrugs are inactive compounds or partially active compounds that yield an active compound upon metabolism in the body, which may or may not be enzymatically controlled. Prodrugs may also be broadly classified into two groups: bioprecursor and carrier prodrugs. Prodrugs may also be subclassified according to the nature of their action. Bioprecursor prodrugs are compounds that already contain the embryo of the active species within their structure, whereby the active species are produced upon metabolism.

Carrier prodrugs are formed by combining the active drug (e.g., active ingredient) with a carrier species forming a compound having desirable chemical and biological characteristics, whereby the link is an ester or amide so that the carrier prodrug is easily metabolized upon absorption or delivery to the target site. For example, lipophilic moieties may be incorporated to improve transport through membranes. Carrier prodrugs linked by a functional group to carrier are referred to as bipartite prodrugs. Prodrugs where the carrier is linked to the drug by a separate structure are referred to as tripartite prodrugs, whereby the carrier is removed by an enzyme-controlled metabolic process, and whereby the linking structure is removed by an enzyme system or by a chemical reaction. A hydroxy-protecting group includes, for example, a tert-butyloxy-carbonyl (t-BOC) and t-butyl-dimethyl-silyl (TBS). Other hydroxy protecting groups contemplated are known in the art.

In another embodiment, a dosage form and/or composition may include one or more active metabolites of the active ingredients in place of or in addition to the active ingredients disclosed herein.

Dosage form compositions containing the active ingredients may also contain one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (for example, anionic, cationic, amphoteric and nonionic), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

As used herein, an oral dosage form may include capsules (a solid oral dosage form consisting of a shell and a filling, whereby the shell is composed of a single sealed enclosure, or two halves that fit together and which are sometimes sealed with a band and whereby capsule shells may be made from gelatin, starch, or cellulose, or other suitable materials, may be soft or hard, and are filled with solid or liquid ingredients that can be poured or squeezed), capsule or coated pellets (solid dosage form in which the drug is enclosed within either a hard or soft soluble container or "shell" made from a suitable form of gelatin; the drug itself is in the form of granules to which varying amounts of coating have been applied), capsule coated extended release (a solid dosage form in which the drug is enclosed within either a hard or soft soluble container or "shell" made from a suitable form of gelatin; additionally, the capsule is covered in a designated coating, and which releases a drug or drugs in such a manner to allow at least a reduction in dosing frequency as compared to that drug or drugs presented as a conventional dosage form), capsule delayed release (a solid dosage form in which the drug is enclosed within either a hard or soft soluble container made from a suitable form of gelatin, and which releases a drug (or drugs) at a time other than promptly after administration, whereby enteric-coated articles are delayed release dosage forms), capsule delayed release pellets (solid dosage form in which the drug is enclosed within either a hard or soft soluble container or "shell" made from a suitable form of gelatin); the drug itself is in the form of granules to which enteric coating has been applied, thus delaying release of the drug until its passage into the intestines), capsule extended release (a solid dosage form in which the drug is enclosed within either a hard or soft soluble container made from a suitable form of gelatin, and which releases a drug or drugs in such a manner to allow a reduction in dosing frequency as compared to that drug or drugs presented as a conventional dosage form), capsule film-coated extended release (a solid dosage form in which the drug is enclosed within either a hard or soft soluble container or "shell" made from a suitable form of gelatin; additionally, the capsule is covered in a designated film coating, and which releases a drug or drugs in such a manner to allow at least a reduction in dosing frequency as compared to that drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), and capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule; typically, the active ingredients are dissolved or suspended in a liquid vehicle).

Oral dosage forms contemplated herein also include granules (a small particle or grain), pellet (a small sterile solid mass consisting of a highly purified drug, with or without excipients, made by the formation of granules, or by compression and molding), pellets coated extended release (a solid dosage form in which the drug itself is in the form of granules to which varying amounts of coating have been applied, and which releases a drug or drugs in such a manner to allow a reduction in dosing frequency as compared to that drug or drugs presented as a conventional dosage form), pill (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), or syrup (an oral solution containing high concentrations of sucrose or other sugars; the term has also been used to include any other liquid dosage form prepared in a sweet and viscid vehicle, including oral suspensions).

Oral dosage forms contemplated herein may further include a tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant after-taste), tablet coated (a solid dosage form that contains medicinal substances with or without suitable diluents and is covered with a designated coating), tablet coated particles (a solid dosage form containing a conglomerate of medicinal particles that have each been covered with a coating), tablet delayed release (a solid dosage form which releases a drug or drugs at a time other than promptly after administration, whereby enteric-coated articles are delayed release dosage forms), tablet delayed release particles (a solid dosage form containing a conglomerate of medicinal particles that have been covered with a coating which releases a drug or drugs at a time other than promptly after administration, whereby enteric-coated articles are delayed release dosage forms), tablet dispersible (a tablet that, prior to administration, is intended to be placed in liquid, where its contents will be distributed evenly throughout that liquid, whereby term 'tablet, dispersible' is no longer used for approved drug products, and it has been replaced by the term 'tablet, for suspension'), tablet effervescent (a solid dosage form containing mixtures of acids, for example, citric acid, tartaric acid, and sodium bicarbonate, which release carbon dioxide when dissolved in water, whereby it is intended to be dissolved or dispersed in water before administration), tablet extended release (a solid dosage form containing a drug which allows at least a reduction in dosing frequency as compared to that drug presented in conventional dosage form), tablet film coated (a solid dosage form that contains medicinal substances with or without suitable diluents and is coated with a thin layer of a water-insoluble or water-soluble polymer), tablet film coated extended release (a solid dosage form that contains medicinal substances with or without suitable diluents and is coated with a thin layer of a water-insoluble or water-soluble polymer; the tablet is formulated in such manner as to make the contained medicament available over an extended period of time following ingestion), tablet for solution (a tablet that forms a solution when placed in a liquid), tablet for suspension (a tablet that forms a suspension when placed in a liquid, which is formerly referred to as a 'dispersible tablet'), tablet multilayer (a solid dosage form containing medicinal substances that have been compressed to form a multiple-layered tablet or a tablet-within-a-tablet, the inner tablet being the core and the outer portion being the shell), tablet multilayer extended release (a solid dosage form containing medicinal substances that have been compressed to form a multiple-layered tablet or a tablet-within-a-tablet, the inner tablet being the core and the outer portion being the shell, which, additionally, is covered in a designated coating; the tablet is formulated in such manner as to allow at least a reduction in dosing frequency as compared to that drug presented as a conventional dosage form), tablet orally disintegrating (a solid dosage form containing medicinal substances which disintegrates rapidly, usually within a matter of seconds, when placed upon the tongue), tablet orally disintegrating delayed release (a solid dosage form containing medicinal substances which disintegrates rapidly, usually within a matter of seconds, when placed upon the tongue, but which releases a drug or drugs at a time other than promptly after administration), tablet soluble (a solid dosage form that contains medicinal substances with or without suitable diluents and possesses the ability to dissolve in fluids), tablet sugar coated (a solid dosage form that contains medicinal substances with or without suitable diluents and is coated with a colored or an uncolored water-soluble sugar), and the like.

Injection and infusion dosage forms (i.e., parenteral dosage forms) include, but are not limited to, the following. Liposomal injection includes or forms liposomes or a lipid bilayer vesicle having phospholipids that encapsulate an active drug substance. Injection includes a sterile preparation intended for parenteral use. Five distinct classes of injections exist as defined by the USP. Emulsion injection includes an emulsion comprising a sterile, pyrogen-free preparation intended to be administered parenterally. Lipid complex and powder for solution injection are sterile preparations intended for reconstitution to form a solution for parenteral use.

Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization.

Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution suitable for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

A parenteral carrier system may include one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

Inhalation dosage forms may include, but are not limited to, aerosol being a product that is packaged under pressure and contains therapeutically active ingredients that are released upon activation of an appropriate valve system intended for topical application to the skin as well as local application into the nose (nasal aerosols), mouth (lingual and sublingual aerosols), or lungs (inhalation aerosols). Inhalation dosage forms further include foam aerosol being a dosage form containing one or more active ingredients, surfactants, aqueous or nonaqueous liquids, and the propellants, whereby if the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged. Inhalation dosage forms may also include metered aerosol being a pressurized dosage form consisting of metered dose valves which allow for the delivery of a uniform quantity of spray upon each activation; powder aerosol being a product that is packaged under pressure and contains therapeutically active ingredients, in the form of a powder, that are released upon activation of an appropriate valve system; and aerosol spray being an aerosol product which utilizes a compressed gas as the propellant to provide the force necessary to expel the product as a wet spray and being applicable to solutions of medicinal agents in aqueous solvents.

Pharmaceutically suitable inhalation carrier systems may include pharmaceutically suitable inactive ingredients known in the art for use in various inhalation dosage forms, such as (but not limited to) aerosol propellants (for example, hydrofluroalkane propellants), surfactants, additives, suspension agents, solvents, stabilizers and the like.

A transdermal dosage form may include, but not limited to, a patch being a drug delivery system that often contains an adhesive backing that is usually applied to an external site on the body, whereby the ingredients either passively diffuse from, or are actively transported from some portion of the patch, and whereby depending upon the patch, the ingredients are either delivered to the outer surface of the body or into the body; and other various types of transdermal patches such as matrix, reservoir and others known in the art. The "pharmaceutically suitable transdermal carrier system" may include pharmaceutically suitable inactive ingredients known in the art for use in various transdermal dosage forms, such as (but not limited to) solvents, adhesives, diluents, additives, permeation enhancing agents, surfactants, emulsifiers, liposomes, and the like.

Suitable dosage amounts and dosing regimens may be selected in accordance with a variety of factors, including one or more particular conditions being treated, the severity of the one or more conditions, the genetic profile, age, health, sex, diet, and weight of the subject, the route of administration alone or in combination with pharmacological considerations including the activity, efficacy, bioavailability, pharmacokinetic, and toxicological profiles of the particular compound employed, whether a drug delivery system is utilized and whether the drug is administered as part of a drug combination. Therefore, the dosage regimen to be employed may vary widely and may necessarily deviate from the dosage regimens set forth herein.

Contemplated dosage forms may include an amount of one or more JAK/STAT pathway inhibitors ranging from about 1 to about 1200 mg, or about 5 to about 100 mg, or about 25 to about 800 mg, or about 100 to about 500 mg, or 0.1 to 50 milligrams (±10%), or 10 to 100 milligrams (±10%), or 5 to 500 milligrams (±10%), or 0.1 to 200 milligrams (±10%), or 1 to 100 milligrams (±10%), or 5 to 50 milligrams (±10%), or 30 milligrams (±10%), or 20 milligrams (±10%), or 10 milligrams (±10%), or 5 milligrams (±10%), per dosage form, such as, for example, a tablet, a pill, a bolus, and the like.

In another embodiment, a dosage form may be administered to a subject in need thereof once per day, or twice per day, or once every 6 hours, or once every 4 hours, or once every 2 hours, or hourly, or twice an hour, or twice a day, or twice a week, or monthly.

The phrase "therapeutically effective" is intended to qualify the amount that will achieve the goal of improvement in disease severity and/or the frequency of incidence over non-treatment, while limiting, reducing, or avoiding adverse side effects typically associated with disease therapies. A "therapeutic effective" amount relieves to some extent one or more of the symptoms of a cancer disease or disorder. In reference to the treatment of a cancer, a therapeutic effect refers to one or more of the following: 1) reduction in the number of cancer cells by, for example, killing the cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anticancer agents. "Therapeutic effective amount" is intended to qualify the amount required to achieve a therapeutic effect.

A therapeutically effective amount of a JAK/STAT pathway inhibitor may be any amount that begins to improve cancer treatment in a subject either administered alone or in combination with another therapeutic agent. In one embodiment, an effective amount of an inhibitor used in the therapeutic regime described herein may be, for example, about 1 mg, or about 5 mg, or about 10 mg, or about 25 mg, or about 50 mg, or about 100 mg, or about 200 mg, or about 400 mg, or about 500 mg, or about 600 mg, or about 1000 mg, or about 1200 mg, or about 1400 mg, or from about 10 to about 60 mg, or about 50 mg to about 200 mg, or about 150 mg to about 600 mg per day. Further, another effective amount of an inhibitor used herein may be that which results in a detectable blood level of above about 1 ng/dL, 5, ng/dL, 10 ng/dL, 20, ng/dL, 35 ng/dL, or about 70 ng/dL, or about 140 ng/dL, or about 280 ng/dL, or about 350 ng/dL, or lower or higher.

The term "pharmaceutically acceptable" is used herein to mean that the modified noun is appropriate for use in a pharmaceutical product. Pharmaceutically acceptable cations include metallic ions and organic ions. Other metallic ions may include, but are not limited to appropriate alkali metal salts, alkaline earth metal salts and other physiological acceptable metal ions. Exemplary ions may include aluminum, calcium, lithium, magnesium, potassium, sodium and zinc in their usual valences. Organic ions may include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Pharmaceutically acceptable acids may include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

It is further contemplated that one active ingredient may be in an extended release form, while an optional second, third, or fourth other active ingredient, for example, may or may not be, so the recipient experiences, for example, a spike in the second, third, or fourth active ingredient that dissipates rapidly, while the first active ingredient is maintained in a higher concentration in the blood stream over a longer period of time. Similarly, one of the active ingredients may be an active metabolite, while another may be in an unmetabolized state, such that the active metabolite has an immediate effect upon administration to a subject whereas the unmetabolized active ingredient administered in a single dosage form may need to be metabolized before taking effect in the subject.

Also contemplated are solid form preparations that include at least one active ingredient which are intended to be converted, shortly before use, to liquid form preparations for oral administration. Such liquid forms may include solutions, suspensions, and emulsions. These preparations may contain, in addition to the active component, colorants, flavors, stabilizers, buffers, artificial and natural sweeteners, dispersants, thickeners, solubilizing agents, and the like. Solutions or suspensions may be applied topically and/or directly to the nasal cavity, respiratory tract, eye, or ear by conventional means, for example with a dropper, pipette or spray.

Alternatively, one or more of the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier may form a gel in the nasal cavity. The powder composition may be presented in unit dose form, for example, in capsules or cartridges of, for example, gelatin, or blister packs from which the powder may be administered by means of an inhaler.

The pharmaceutical preparations may be in unit dosage forms. In such form, the preparation may be subdivided into unit doses containing appropriate quantities of the active component. The unit dosage form can be a packaged preparation, such as a kit or other form, the package containing discrete quantities of preparation, such as packeted tablets, capsules, liquids or powders in vials or ampoules. Also, the unit dosage form can be a capsule, tablet, cachet, or lozenge, or it can be the appropriate number of any of these in packaged form.

The present disclosure is further illustrated by the following examples, which should not be construed as limiting in any way. The practice of the present invention will employ, unless otherwise indicated, conventional techniques of pharmacology and pharmaceutics, which are within the skill of the art.

EXAMPLES

Materials and Methods

Cell Culture and Growth Assays

Cell lines were from the American Type Culture Collection (Rockville, Md.), except for CWR-R1 and CWR-22RV1 cells, which were kindly provided by Dr. Donald VanderGriend, the University of Chicago.

These cell lines were characterized for relative radioresistance using a clonogenic assay. Briefly, the cells were cultured in their appropriate media at 5% CO2 at 37° C. Optimal cell plating concentrations for a p60 dish were determined for each cell line. The majority of cell lines were plated in triplicate at concentrations of 100 cells/plate for control, 1000 cells/plate for 2 Gy, 2000 cells/plate for 5 Gy, and 3000 cells/plate for 8 Gy. Plates were irradiated 24 hours after plating with either 2, 5, or 8 Gy using a irradiated using a Nordion Gammacell $^{60}$Co irradiator operating at a dose rate of ~18 Gy/minute. Cells were allowed to grow for 10-21 days (depending on the cell line) until colonies were >50 cells. Plates were then fixed with formalin and stained with crystal violet. Colonies with more than 50 cells were counted. Clonogenic survival for Clonogenic data was obtained for all cell lines tested in screen.

Plasmids

All genes were cloned in pQCXIP plasmid (Clontech, Palo Alto, Calif.). Stable knock-downs were generated with pLKO.1 plasmid (Sigma-Aldrich, St Luis, Mo.; see Khodarev et, al., STAT1 pathway mediates amplification of metastatic potential and resistance to therapy. PLoS One. 2009 Jun. 8; 4(6):e5821)

Transfections

Forty percent (40%) confluent cells were transfected 0.1-1 µg of plasmids using Oligofectamine (Invitrogen, Carlsbad, Calif., USA) or Fugene (Roche) as we previously described (Khodarev et. al., Cooperativity of the MUC1 oncoprotein and STAT1 pathway in poor prognosis human breast cancer. Oncogene. 2010 Feb. 11; 29(6):920-9). Transfection efficiency was optimized and estimated to be between 10% and 90% depending on the cell type.

Transcription Assays Real-Time PCR Analysis cDNA was synthesized as described previously (see, Khodarev N N, Yu J, Nodzenski E, et al. Method of RNA purification from endothelial cells for DNA array experiments. Biotechniques 2002; 32: 316-20). For the internal control, GAPDH was used. PCR was done for 40 cycles at 95° C. for 15 s and 60° C. for 1 min after initial incubations at 50° C. for 2 min and 95° C. for 10 min using SYBR Green PCR reagent in ABI 7700 System (Applied Biosystems). ∆Ct values were calculated according to the manufacturer's instructions. Fold induction/suppression relative to GAPDH was calculated as $2^{-\Delta Ct}$. Fold induction of gene $X_{si}$ in gene-specific siRNA transfected cell line relative to gene $X_{nt}$ in the same cell line transfected by non-targeting siRNA was calculated as $2^{-(\Delta\Delta CtX)}$, where ∆Ct values of all control replicates were averaged. Number of replicates per each group varied from three to six in different experiments.

Cell Extraction, Immunoprecipitation and Western Blotting

Total cellular protein was extracted in radioimmunoprecipitation assay buffer with protease inhibitors added (1×PBS, 1% NP40, 0.5% sodium deoxycholate, 0.1% SDS, 1 mmol/L $Na_3VO_4$, 2 µg/mL aprotinin, 1 mmol/L phenylmethylsulfonyl fluoride). All samples were normalized by protein concentration using Bradford reagent and standard solution of bovine serum albumin (1 mg/mL). Concentration of all samples was adjusted to 1 mg/mL and equal amount of protein was loaded in each well. For total proteins, 10 µg of protein was loaded per well. Proteins were separated on 7.5%-12% SDS-PAGE (depending on molecular mass of protein) and transferred to polyvinylidene difluoride membranes (PVDF). Total proteins were detected using the rabbit or goat primary Abs. For loading control, the antibodies for actin (I-19) and glyceraldehyde-3-phosphate dehydrogenase (GAPDH; FL-335) were used. All antibodies were purchased from Santa Cruz Biotechnology. Images were quantified with ImageJ software by integration pixel values across the area of specific bands.

Antibodies

Western Blots were probed using antibodies at 1:1000 unless stated otherwise. All antibodies were purchased from Santa Cruz Biotechnology.

Example 1. JAK/STAT Survival Pathway for Metastatic Castrate Resistant Prostate Cancer (mCRPC)

Determine JAK/STAT Pathway Survival Mechanisms Specific to Prostate Cancer

In Vivo Radiotherapy of Prostate Cancer Cells Leads to Upregulation of JAK/STAT Pathways.

To determine whether the observations regarding upregulation of the JAK/STAT pathway following radiotherapy previously identified in other malignancies are also relevant in prostate cancer, we performed gene profiling experiments using Affymetrix microarrays on PC3 prostate cancer mouse xenografts prior to and following irradiation. Methods of xenograft experiments and DNA array analysis were described by us in detail previously (Kimchi E T et. al, Progression of Barrett's metaplasia to adenocarcinoma is associated with the suppression of the transcriptional programs of epidermal differentiation. Cancer Res. 2005 Apr. 15; 65(8):3146-54; Khodarev N N et al., Signal transducer and activator of transcription 1 regulates both cytotoxic and prosurvival functions in tumor cells. Cancer Res. 2007 Oct. 1; 67(19):9214-20.). Differential gene expression analysis was performed using standard SAM analysis with a false discovery rate of 5%.

This gene set was subsequently analysed using Ingenuity Pathway Analysis software, which highlighted the importance of the JAK/STAT signalling in the radiation response of prostate cancer. Based on the analyses of activated down-stream genes one of the potential up-stream regulator is IL6 and IFN-gamma, which through activation of JAK kinases involve STAT3, STAT2 and IRF1/IRF8 genes. Another important node is STAT1/STAT2 activation being linked to the greatest number of differentially up-regulated genes following radiotherapy (FIG. 1).

Figure 3:
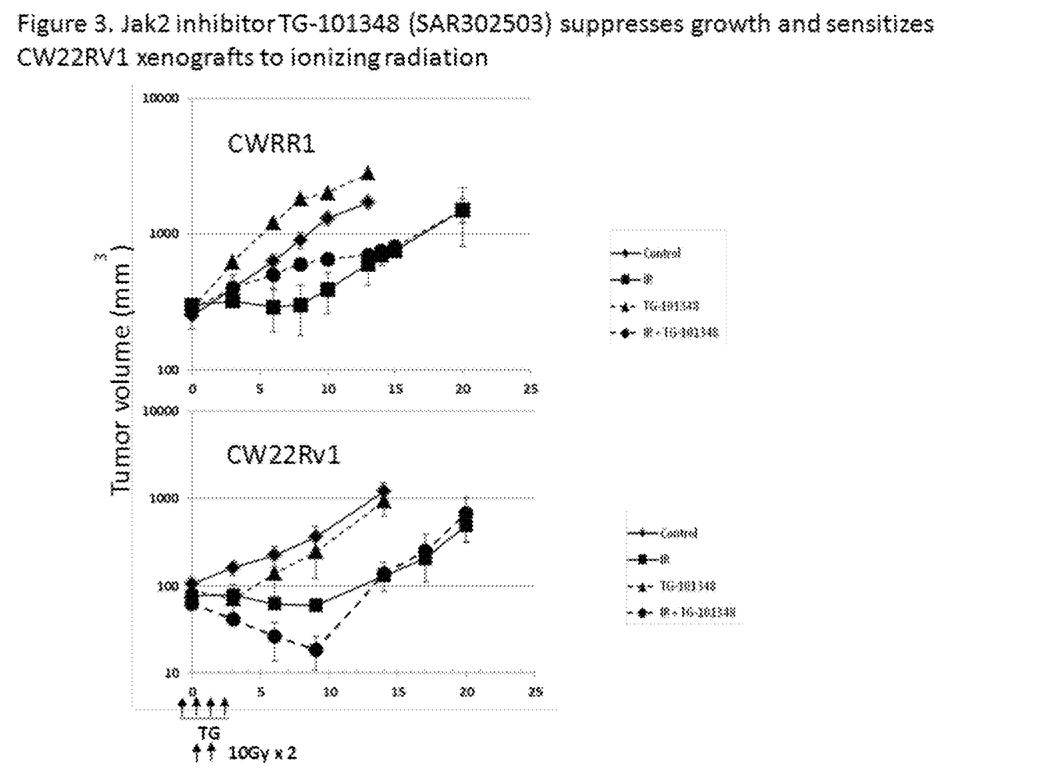
FIG. 3 shows the effect of JAK2 inhibitor SAR302503 in prostate cancer xenografts treated with gamma radiation.

The aforementioned data suggest that STAT1, STAT2 and/or STAT5 are most relevant to advanced prostate cancer. To determine the potential therapeutic value of targeting the JAK/STAT pathway in prostate cancer, the cells were exposed to the specific JAK2 inhibitor SAR302503. Since it is expected that the greatest value of inhibiting the JAK/STAT pathway is in combination with other toxic insults we evaluated the effect of ionizing radiation used in the treatment of CRPC, and SAR302503 in the genetically related CWR lines (FIG. 2). Cells were plated in p60 dishes with or w/o 0.5 µM of SAR302503 and irradiated with 2 or 5 Gy (or left un-irradiated). Colonies counting and estimation of survival fractions were performed as described elsewhere (Khodarev et. al., 2007, Cancer Research). We found that CWR-R1 is more resistant to IR compared to CWR-22RV1 and cytotoxic activity of IR is not enhanced by the JAK2 specific inhibitor SAR302503. However, effects of IR were significantly enhanced in CWR-22RV1 cell line (see FIG. 2). Therefore these data indicated that SAR302503 can potentiate cytotoxic effects of IR in prostate cancer cells. To extend these observations in preclinical animal models we established xenografts of CWR-R1 and CWR-22RV1. For this purpose $10^7$ cells were injected in the right flank of each nude mice (5 animals per group) and when tumors reached 200 mm$^3$ in volume mice were either left un-treated, or treated with SAR302503 (120 mg/kg, once a day, 4 days) or irradiated locally (2×10 Gy) or subjected to combined treatments with SAR302503 and IR. As is shown in FIG. 3 combined treatment of CWR-22RV1 tumors with SAR302503 and IR led to the significant suppression of tumor growth by day 9 after beginning of treatment. At the same tumors treatment by SAR302503 alone led to the 4-days growth delay compared with control tumors. These effects were not observed in CWRR1. Molecular differences between two tumors are currently under investigation. The difference between CWR-R1 and CWR-22RV1 is especially noteworthy since they are isogenic, castrate resistant, and carry both native and splice variant androgen receptor, which is reminiscent of the findings in human prostate cancer specimens.

MCL1 is a Significant Downstream Mediator of the JAK/STAT Survival Pathway in Prostate Cancer Cells To better understand the relevant partners of the JAK/STAT survival pathway specifically in prostate cancer, CWR-R1 and CWR-22RV1 cells were tested with gamma radiation after transfection with a panel of 86 siRNA's to previously reported members of the JAK/STAT signaling pathway. The final screen was conducted as follows: On day 1, Lipofectamine RNAiMAX 0.075 µL/well diluted in Opti-MEM (Life Technologies) was added using a Tecan Freedom EVO 200 robotic liquid handling station to previously prepared 384-well microplates (Corning/3712) containing immobilized pooled siRNAs (Dharmacon siGENOME) plated in triplicate for each target gene. Cells were then added using a Thermo Electron MultiDrop Combi dispenser at 500 cells/well in 50 µL of RPMI 1640 media supplemented with 10% FCS. The final siRNA concentration in each well was 50 nM. Plates were be incubated overnight at 37° C., and on day 2 were treated with ionizing radiation at a dose of either 3 Gy or left untreated. Plates were incubated at 37° C. and then assayed for viability on days 3 and 4 using the highly sensitive luciferase-based CellTiterGlo assay (Promega, Madison, Wis.). Luminescent reagent was added using a Thermo Electron MultiDrop Combi, and luminescent measurements was taken 90 minutes later using Molecular Devices Analyst GT.

Figure 4:
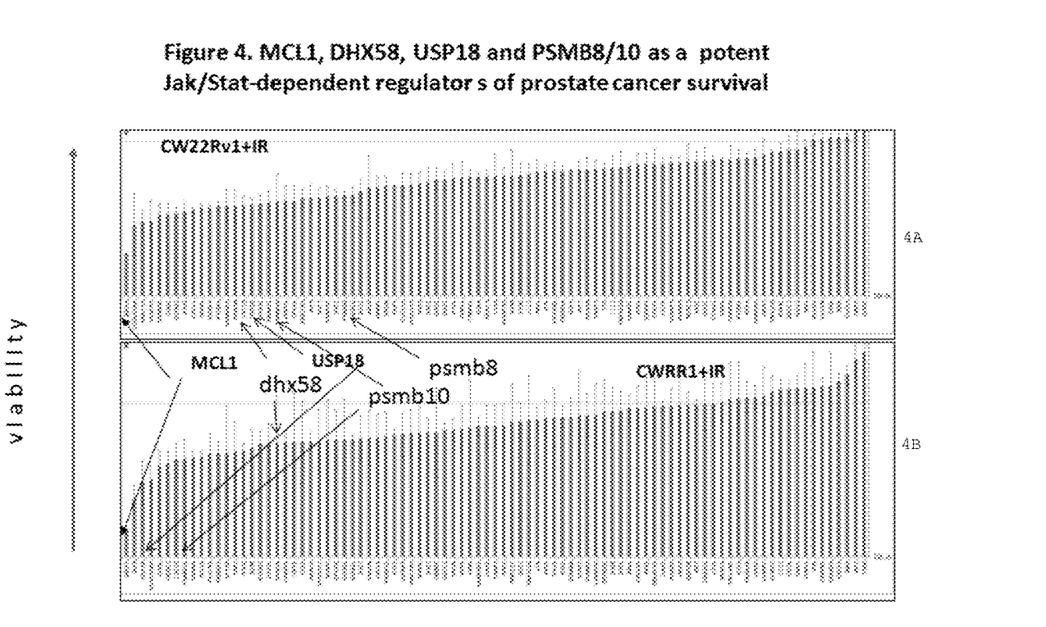
FIG. 4 (presented as FIGS. 4A and 4B) shows that expression of MCL1, USP18, DHX58 (LGP2) and PSMB8 and 10 confers post-radiation survival of prostate cancer cell lines CWRR1 and CW22Rv1. Table No. 1, below, lists the genes presented in FIG. 4 (FIGS. 4A and 4B).

The siRNA potentiating cytotoxicity to the greatest degree inhibited the anti-apoptotic BCL2 family member MCL1 (see FIG. 4.). The below table, Table No. 1, lists the genes presented in FIG. 4 (FIGS. 4A and 4B). This is different than in cell lines derived from other malignancies for which MCL1 is not one of the top 10 genes selected. As noted above, MCL1 is recognized as one of the most common oncogenes amplified in various cancers, including prostate cancer (Beroukhim R, Mermel C H, Porter D, et al: The landscape of somatic copy-number alteration across human cancers. Nature 463:899-905, 2010). This suggests that the JAK/STAT→MCL1 pathway is uniquely important to prostate cancer, and MCL1 may be an additional therapeutic target. In addition to that apical suppressor of RNA-dependent IFN-beta production DHX58 (LGP2), IFN-dependent isopeptidase USP18 and proteosome subunits PSMB8 and PSMB10 were among genes which suppression significantly suppressed viability of prostate cancer cell lines. These genes can also be used as additional down-stream targets but besides their expression can be associated with sensitivity of the individual prostate tumors to SAR302503.

TABLE NO. 1

List of genes presented in FIG. 4 (presented as FIGS. 4A and 4B)

| FIG. 4A<br>CW22Rv1 + IR | FIG. 4B<br>CWRR1 + IR |
|---|---|
| MCL1 | MCL1 |
| LGALS3BP | IRF9 |
| RNF213 | USP18 |
| PLSCR1 | LGALS3BP |
| DDX60L | OASL |
| OASL | HERC5 |
| IFITM3 | CXCL9 |
| IFIH1 | PSMB10 |
| CXCL1 | DDX60 |
| WARS | ISG15 |
| DDX60 | PLSCR1 |
| IFITM1 | TRIM21 |
| SAMHD1 | SP110 |
| DHX58 | TAP1 |
| CXCL9 | IFIH1 |
| USP18 | B2M |
| DTX3L | IFITM3 |
| TRIM21 | DTX3L |
| PSMB10 | DHX58 |
| EPSTI1 | VAMP5 |
| SP110 | GBP1 |
| PRIC285 | CCL2 |
| IRF9 | HERC6 |
| IFI27 | TPD52L1 |
| PARP12 | WARS |
| IFIT2 | EPSTI1 |
| PSMB8 | IFITM1 |
| HERC6 | IFITM2 |
| BST2 | IFI27 |
| MGP | TAGLN |
| HNMT | CXCL1 |
| SRGN | PARP12 |
| TAP1 | IFIT3 |
| CXCL10 | IGFBP3 |
| TPD52L1 | PRIC285 |
| IFI35 | IFI44L |
| XAF1 | IFI35 |
| OAS1 | HNMT |
| DAZ1 | ABCC3 |
| IFI16 | SRGN |
| THBS1 | RTP4 |
| CMPK2 | LY96 |
| IFI44 | SAMHD1 |
| HERC5 | OAS1 |
| CTSS | TIMP3 |
| MARCKS | XAF1 |
| B2M | RNF213 |
| LY96 | BST2 |
| CCL5 | TNFSF10 |
| MX1 | LTK |
| IFI6 | MGP |
| EIF2AK2 | DAZ1 |
| TRIM14 | IFIT2 |
| IFIT1 | PSMB8 |
| IRF7 | STAT1 |
| DDX58 | PSMB9 |
| TIMP3 | SAMD9L |
| LTK | DDX60L |
| CCL2 | IFI44 |
| TNFSF10 | IFIT1 |
| LAMP3 | MX1 |
| IFIT3 | CXCL10 |
| IGFBP3 | MX2 |
| STAT1 | MARCKS |
| CD74 | OAS3 |
| VAMP5 | RSAD2 |
| PSMB9 | UBA7 |
| NLRC5 | DDX58 |
| MX2 | IRF7 |
| OAS3 | UBE2L6 |
| CCNA1 | CTSS |
| GBP1 | NLRC5 |
| SAMD9 | EIF2AK2 |
| IFITM2 | IFI6 |
| RTP4 | TRIM14 |

TABLE NO. 1-continued

List of genes presented in FIG. 4 (presented as FIGS. 4A and 4B)

| FIG. 4A<br>CW22Rv1 + IR | FIG. 4B<br>CWRR1 + IR |
|---|---|
| SAMD9L | OAS2 |
| UBA7 | LAMP3 |
| UBE2L6 | CCNA1 |
| IFI44L | CCL5 |
| ABCC3 | CD74 |
| ISG15 | GBP2 |
| IRF1 | THBS1 |
| RSAD2 | IFI6 |
| TAGLN | CMPK2 |
| LY6E | SAMD9 |
| NMI | CXCL3 |
| CXCL3 | NMI |
| GBP2 | IRF1 |
| OAS2 | LY6E |

The invention has been described in an illustrative manner and it is to be understood the terminology used is intended to be in the nature of description rather than of limitation. All patents and other references cited herein are incorporated herein by reference in their entirety. It is also understood that many modifications, equivalents, and variations of the present disclosure are possible in light of the above teachings. Therefore, it is to be understood that within the scope of the appended claims, the invention may be practiced other than as specifically described.

We claim:

1. A method of treating a subject with a chemoresistant and/or radioresistant prostate cancer, comprising:
    administering a therapeutically effective amount of a selective inhibitor of JAK2,
    wherein the therapeutically effective amount of the selective inhibitor of JAK2 suppresses growth of the chemoresistant and/or radioresistant prostate cancer, and
    wherein the selective inhibitor of JAK2 is SAR302503.

2. The method of claim 1, wherein the prostate cancer has an amplified level of expression of MCL1, DHX58, PSMB8, PSMB9, or PSMB10 compared to a normal control cell.

3. The method of claim 1 further comprising administering to the subject a therapeutically effective amount of at least one of an antineoplastic agent or a radiotherapy.

4. The method of claim 3, wherein the radiotherapy comprises at least one of brachytherapy, external beam radiation therapy, or radiation from cesium, iridium, iodine, or cobalt.

5. The method of claim 1 further comprising administering a second selective inhibitor of the JAK/STAT pathway.

6. A method of treating a subject with a metastatic castrate-resistant prostate cancer, comprising:
    administering a therapeutically effective amount of a selective inhibitor of JAK2 to the subject,
    wherein the administration of the therapeutically effective amount of the selective inhibitor of JAK2 suppresses growth of the metastatic castrate-resistant prostate cancer, and
    wherein the selective inhibitor of JAK2 is SAR302503.

7. The method of claim 6 further comprising administration of a second selective inhibitor of JAK2, wherein the second selective inhibitor of JAK2 comprises one or more of CYT387, SB1518, CEP701, and LY2784544.

8. The method of claim 7, wherein the therapeutically effective amount of SAR302503 is an amount less than that which causes myelosuppression.

9. The method of claim 6 further comprising administering a therapeutically effective amount of a taxane or a derivative thereof, an androgen receptor inhibitor or mediator, or a combination thereof.

10. The method of claim 9, wherein the taxane or the derivative thereof is paclitaxel, docetaxel, or cabazitaxel.

11. The method of claim 9, wherein the androgen receptor inhibitor or mediator is cyperterone, flutamide, nilutamide, enzalutamide, bicalutamide, a peptide antiandrogen; RU58642, LG120907, LG105, RD162, BMS-641988, CH5137291, ataric acid, N-butylbensensulfonamide, enobosarm, BMS-564,929, LGD-4033, AC-262,356, LGD-3303, S-40503, andarine, or S-23.

12. A method of treating a subject with a metastatic castrate-resistant prostate cancer, comprising:
    administering a therapeutically effective amount of a selective inhibitor of JAK2; and
    administering a therapeutically effective amount of a radiotherapy,
    wherein the administration of the therapeutically effective amount of the selective inhibitor of JAK2 suppresses growth of the metastatic castrate-resistant prostate cancer, and
    wherein the selective inhibitor of JAK2 is SAR302503.

13. The method of claim 12, wherein the therapeutically effective amount of the radiotherapy suppresses growth of the metastatic castrate-resistant prostate cancer.

14. The method of claim 12 further comprising administering to the subject a therapeutically effective amount of an antineoplastic agent.

15. The method of claim 14, wherein the antineoplastic agent comprises a taxane or a derivative thereof.

16. The method of claim 15, wherein the taxane or the derivative thereof is paclitaxel, docetaxel, or cabazitaxel.

17. The method of claim 12, wherein the radiotherapy comprises at least one of brachytherapy, external beam radiation therapy, or radiation from cesium, iridium, iodine, or cobalt.

* * * * *